United States Patent [19]
Davis

[11] Patent Number: 5,171,321
[45] Date of Patent: Dec. 15, 1992

[54] NIPPLE PROSTHESIS AND METHOD OF MAKING THE SAME

[76] Inventor: Joseph P. Davis, 11632 Newbridge Ct., Reston, Va. 22091

[21] Appl. No.: 848,060

[22] Filed: Mar. 9, 1992

[51] Int. Cl.⁵ ................................ A61F 2/52
[52] U.S. Cl. .......................... 623/7; 623/8; 128/890
[58] Field of Search ............... 623/7, 8; 128/890

[56] References Cited

U.S. PATENT DOCUMENTS

| | | | |
|---|---|---|---|
| 814,181 | 3/1906 | Wolfe | 623/7 |
| 2,364,866 | 7/1941 | Meynier, Jr. | 128/890 |
| 3,285,247 | 11/1966 | Morin | 623/7 |
| 4,127,128 | 11/1978 | Schmidt . | |
| 4,199,825 | 4/1980 | Knoche | 623/7 |
| 4,227,536 | 10/1980 | Shimenkov et al. . | |
| 4,241,737 | 12/1980 | Schmidt . | |
| 4,364,880 | 12/1982 | Howse . | |
| 4,401,492 | 8/1983 | Pfrommer . | |
| 4,573,999 | 3/1986 | Netto | 623/7 |
| 4,701,230 | 10/1987 | Loi . | |
| 4,778,465 | 10/1988 | Wilkins | 623/7 |
| 4,870,977 | 10/1989 | Imonti | 623/7 |
| 5,035,758 | 7/1991 | Degler et al. . | |
| 5,066,302 | 11/1991 | Rice | 623/7 |

FOREIGN PATENT DOCUMENTS 2742394  3/1979  Fed. Rep. of Germany .......... 623/7

Primary Examiner—David Isabella
Assistant Examiner—Gina M. Gualtieri

[57] ABSTRACT

Areola and nipple prosthesis device for application to the surface of a human breast comprising an areola portion having an inner concave surface which conforms to the shape of a human breast to which it is applied and an outer convex surface. The inner concave surface includes an adhesive for removably positioning the prosthesis to the human breast. The nipple portion of the device is disposed proximate to the center of areola portion and extends outwardly from the outer surface of the areola portion.

17 Claims, 2 Drawing Sheets

NIPPLE PROSTHESIS AND METHOD OF MAKING THE SAME

BACKGROUND OF THE INVENTION

1. Field of The Invention

The present invention relates to a prosthetic device and more particularly, to a prosthetic device which simulates a nipple and areola. A method of making the device is also described.

2. Description of the Prior Art

In an effort to improve their appearance and sexuality, women have utilized a variety of techniques, tools and devices to enlarge, harden, and re-shape their breasts and nipples. One common procedure for breast enlargement and augmentation involves surgical implants made from silicone gel and the like. Implants which simulate areolas and nipples also exist in the art. U.S. Pat. No. 4,778,465 to Wilkens is an example of a surgically implantable areola and nipple prosthesis. Such implantable prosthetic devices have become increasingly disfavored as a result of mounting evidence suggesting that they pose health risks such as preventing accurate tumor detection or adversely affecting the autoimmune system. In fact, in early 1992, the U.S. Food and Drug Administration issued a temporary ban on certain breast implant devices pending a more complete analysis of their safety. Such actions have lowered consumer confidence in surgical breast implants of all types. Another disadvantage of implanted prosthetic devices is that once surgically inserted, the wearer must undergo an expensive andsometime dangerous surgical procedure to have the device removed in the event of a defect of the implant.

Simulated nipple devices which are not implanted surgically also exist in the art. U.S. Pat. Nos. 4,127,128 and 4,241,737 to Schmidt are representative of such devices. These devices comprise a built-in component of a brassiere. A key disadvantage of these devices is that they have neither the appearance nor the feel of a natural nipple to either the wearer or to observers. Moreover, such devices are of little use to the increasing number of women who prefer the so-called "natural" or "bra-less" look. Additionally, there are marketing disadvantages to selling simulated nipple devices as a built-in component of a brassiere. Such garments cannot easily be sold in vending machines or in novelty shops

OBJECTS AND SUMMARY OF THE INVENTION

In view of the foregoing limitations and shortcomings of the prior art devices, as well as other disadvantages not specifically mentioned above, it should be apparent that there still exists a need in the art for a prosthetic nipple which overcomes the aforesaid disadvantages.

It is, therefore, a primary object of this invention to fulfill that need by providing a prosthetic nipple and areola which improves the attractiveness and sexuality of the wearer. More specifically, it is an object of this invention to provide a nipple prosthesis which is attached directly tothe skin surface and readily removable so it can be re-used at a later time, if desired.

Another object of the present invention is to provide a prosthetic nipple and areola which does not interfere with mamographies and other diagnostic evaluations.

Yet another object of the present invention is to provide a prosthetic nipple and areola which has the look and feel of natural tissue and skin.

Still another object of the present invention is to provide a prosthetic nipple which can be packaged to be sold in a vending machine or the like.

Yet another object of the present invention is to provide a prosthetic nipple which can be inexpensively manufactured.

Still another object of the present invention is to provide a prosthetic nipple which can be used as a novelty or amusement device.

Yet another object of the present invention is to provide a prosthetic nipple which can be easily removed at the discretion of the user.

Briefly described, the aforementioned objects are accomplished according to the invention by providing a molded areola and nipple prosthesis having the shape, texture, feel, color, and appearance, of a natural, large, firm areola and nipple. The present invention is constructed by conventional molding techniques, thereby allowing it to be made inexpensively.

The device is preferably formed of a resilient plastic, such as, silicone, polyurethane, or natural rubber, polyvinylchloride, polyethylene, polypropylene. Colorant and flavorants can also be added to promote aesthetic and sensual properties. In addition, the device may be made of natural polymeric substances, such as, polysaccharides, which may or may not be edible. Various colors and or sparkles can be applied to the molded article to heighten the interest of the wearer or an observer.

In addition to being a cosmetic device, the invention can be used for novelty and amusement purposes and can be packaged and sold accordingly. In use, the device is attached directly on the skin surface of the breast by suction, by use of a suitable adhesive, or of any other suitable attaching means, thereby avoiding the need for surgical implantation or the use of a brassiere.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
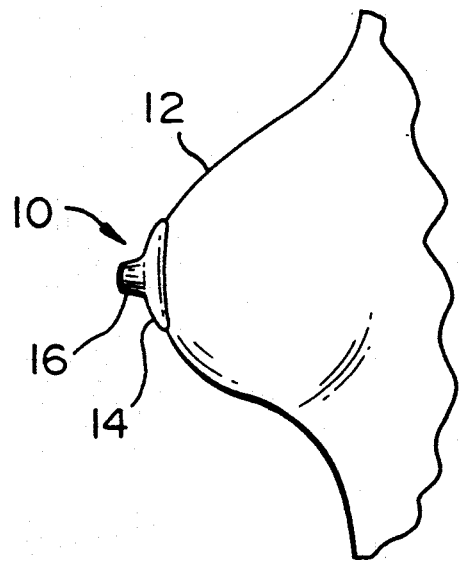
FIG. 1 is an environmental view of the areola and nipple prosthesis of the present invention shown attached to a breast.

Referring now in detail to the drawings wherein like parts are designated by like reference numerals throughout, there is illustrated in FIG. 1 an environmental view of the present invention, designated generally by reference number 10 shown attached to a breast 12.

Figure 2:
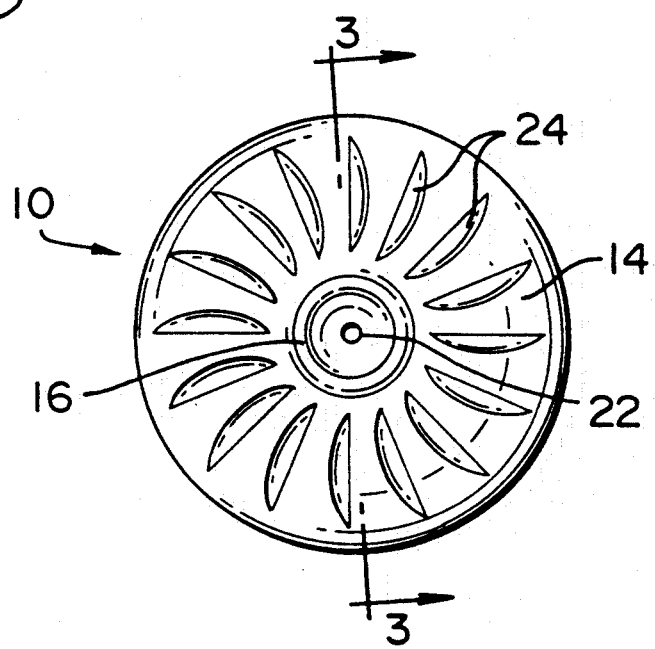
FIG. 2 is a front elevation view of the areola and nipple prosthesis of the present invention.
Figure 3:
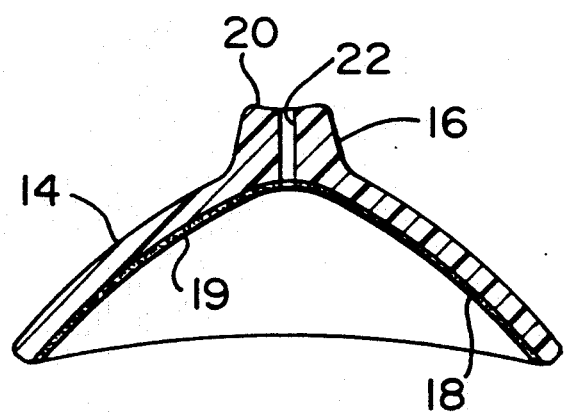
FIG. 3 is a sectional view taken along line 3—3 of FIG. 2.
Figure 4:
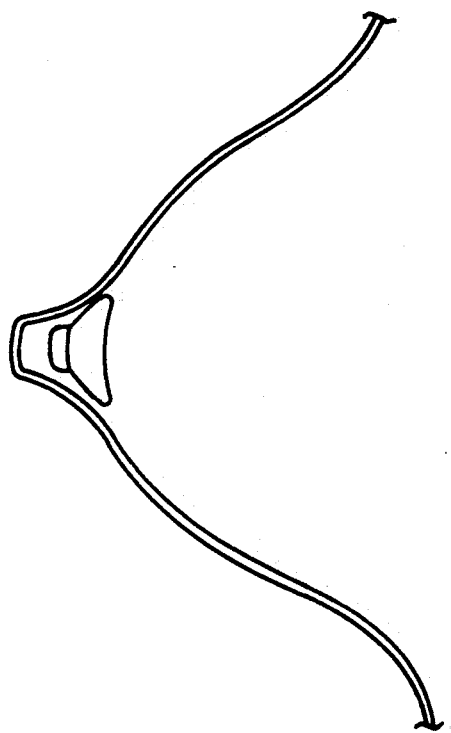
FIG. 4 is a side elevation view, partly in section of an implanted nipple prosthesis known in the prior art.

Prosthetic device 10 is generally comprised of an areola portion 14 and a nipple portion 16 integrally connected to the areola and protruding therefrom. With reference to FIGS. 2 and 3, areola 14 is generally cylindrical having a concave inner surface 18 which is shaped to conform to the approximate curvature of a typical breast. Inner surface 18 is provided with an adhesive layer 19 such as the adhesive used on Band-Aid ® brand adhesive bandages or any other adhesive which can be removed without irritating the skin. The opposite side of the areola is generally convex. To more clearly resemble the natural areola, the convex side of areola 14 is provided with a plurality of small groves 24. Integrally connected to areola portion 14 and protruding outwardly therefrom is nipple portion 16. The nipple portion is generally cylindrically shaped. A slight indentation 20 is provided on the top of nipple 16. Air hole 22 is preferably provided in nipple 16 to render the device more breathable.

Device 10 is preferably constructed of a soft and flexible polyvinylchloride but may alternatively be constructed of material which is dermatologically compatible, soft and resilient. Such materials well known include natural and synthetic, polymers, silicone rubber, polyurethane, polyethylene, polypropylene and the like. The device may be skin colored to appear to be natural when viewed through a see-through blouse.

Device 10 is preferably packaged with a peel-off paper backing (not shown) removably mounted to the adhesive layer 19 on the inner surface 18. Thus, the user need only remove the backing and affix the device directly on the breast.

The method for carrying out the invention is preferably a molding method using male and female molds. Heated polyvinylchloride is poured or injected into the mold, allowed to cool and then removed. Suitable molding techniques are described in U.S. Pat. No. 4,364,880, U.S. Pat. No. 5,035,758 and especially U.S. Pat. No. 4,701,230, the subject matter of each being incorporated herein by reference.

It has been found that the preferred dimensions of the device 10 is for the areola portion 14 to have a diameter of about two inches, and for the nipple portion 16 to have a length and diameter of about ½ inch.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An areola and nipple prosthesis device for application to an outer surface of a human breast comprising:
   an areola portion having an inner concave surface which conforms to a shape of a human breast and an outer convex surface, said inner concave surface including means for removably positioning said prosthesis to the human breast;
   a nipple portion disposed proximate to a center of said areola portion and extending outwardly from said outer surface of said areola portion said convex outer surface of said areola portion being provided with a plurality of radial grooves to simulate a natural areola.

2. The device of claim 1 wherein said nipple portion is integrally connected to said areola portion.

3. The device of claim 2 wherein said device is constructed of a resilient natural or synthetic polymer.

4. The device of claim 4 wherein said nipple portion is provided with a hole disposed longitudinally therethrough to allow air to pass from an outer skin surface to the atmosphere.

5. The device of claim 1 and further comprising an indentation on the top surface of said nipple portion.

6. The device of claim 4 wherein said areola portion has a diameter of about two inches.

7. The device of claim 4 wherein said nipple portion has a length and diameter of about ½ inch.

8. The device of claim 1 wherein said areola portion has a diameter of about two inches.

9. The device of claim 8 wherein said nipple portion has a length and diameter of about ½ inch.

10. The device of claim 1 where the removable positioning means comprise an adhesive.

11. The device of claim 1 where the removable positioning means comprise an adhesive.

12. The device of claim 4 where the removable positioning means comprise an adhesive.

13. The device of claim 9 where the removable positioning means comprise an adhesive.

14. The device of claim 10 further comprising a peel-off layer secured to said adhesive.

15. The device of claim 1 constructed of an edible material.

16. The device of claim 1 wherein said concave surface includes sparkles.

17. The device of claim 1 wherein said concave surface is skin colored.

* * * * *